United States Patent
Heerding

(10) Patent No.: US 7,414,040 B2
(45) Date of Patent: Aug. 19, 2008

(54) THROMBOPOIETIN MIMETICS

(75) Inventor: Dirk A. Heerding, Collegeville, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 588 days.

(21) Appl. No.: 10/516,988

(22) PCT Filed: Jun. 6, 2003

(86) PCT No.: PCT/US03/17837

§ 371 (c)(1), (2), (4) Date: Dec. 6, 2004

(87) PCT Pub. No.: WO03/103686

PCT Pub. Date: Dec. 18, 2003

(65) Prior Publication Data

US 2005/0234020 A1    Oct. 20, 2005

Related U.S. Application Data

(60) Provisional application No. 60/386,694, filed on Jun. 6, 2002, provisional application No. 60/463,241, filed on Apr. 16, 2003.

(51) Int. Cl.
*C07D 231/20*  (2006.01)
*A61K 31/655* (2006.01)
*A61K 31/415* (2006.01)

(52) U.S. Cl. ............. 514/150; 534/753; 534/775; 534/792; 548/183; 548/366.1; 560/20; 560/43; 564/461

(58) Field of Classification Search ........ 514/150; 534/753, 775, 792; 548/183, 366.1; 560/20, 560/43; 564/461
See application file for complete search history.

(56) References Cited

U.S. PATENT DOCUMENTS 2,132,193 A * 10/1938 Schuster et al. ........ 548/366.1
3,728,115 A *  4/1973 Poot et al. ............... 430/196
4,948,900 A    8/1990 Iijima et al.
7,160,870 B2 * 1/2007 Duffy et al. ............. 514/150

FOREIGN PATENT DOCUMENTS

WO   WO-01/89457   * 11/2001

* cited by examiner

*Primary Examiner*—Fiona T Powers
(74) *Attorney, Agent, or Firm*—Wayne J. Dustman; Stephen Venetianer; Charles M. Kinzig

(57) ABSTRACT

Invented are non-peptide TPO mimetics. Also invented are novel processes and intermediates used in the preparation of the presently invented compounds. Also invented is a method of treating thrombocytopenia, in a mammal, including a human, in need thereof which comprises administering to such mammal an effective amount of a selected hydroxy-1-azobenzene derivative.

22 Claims, No Drawings

THROMBOPOIETIN MIMETICS

This application claims the benefit of U.S. Provisional Application Nos. 60/463,241 filed Apr. 16, 2003 and 60/386,694 filed Jun. 6, 2002.

FIELD OF THE INVENTION

This invention relates to thrombopoietin (TPO) mimetics and their use as promoters of thrombopoiesis and megakaryocytopoiesis.

BACKGROUND OF THE INVENTION

Megakaryocytes are bone marrow-derived cells, which are responsible for producing circulating blood platelets. Although comprising <0.25% of the bone marrow cells in most species; they have >10 times the volume of typical marrow cells. See Kuter et al. *Proc. Natl. Acad. Aci. USA* 91: 11104-11108 (1994). Megakaryocytes undergo a process known as endomitosis whereby they replicate their nuclei but fail to undergo cell division and thereby give rise to polyploid cells. In response to a decreased platelet count, the endomitotic rate increases, higher ploidy megakaryocytes are formed, and the number of megakaryocytes may increase up to 3-fold. See Harker *J. Clin. Invest.* 47: 458-465 (1968). In contrast, in response to an elevated platelet count, the endomitotic rate decreases, lower ploidy megakaryocytes are formed, and the number of megakaryocytes may decrease by 50%.

The exact physiological feedback mechanism by which the mass of circulating platelets regulates the endomitotic rate and number of bone marrow megakaryocytes is not known. The circulating thrombopoietic factor involved in mediating this feedback loop is now thought to be thrombopoietin (TPO). More specifically, TPO has been shown to be the main humoral regulator in situations involving thrombocytopenia. See, e.g., Metcalf Nature 369:519-520 (1994). TPO has been shown in several studies to increase platelet counts, increase platelet size, and increase isotope incorporation into platelets of recipient animals. Specifically, TPO is thought to affect megakaryocytopoiesis in several ways: (1) it produces increases in megakaryocyte size and number; (2) it produces an increase in DNA content, in the form of polyploidy, in megakaryocytes; (3) it increases megakaryocyte endomitosis; (4) it produces increased maturation of megakaryocytes; and (5) it produces an increase in the percentage of precursor cells, in the form of small acetylcholinesterase-positive cells, in the bone marrow.

Because platelets (thrombocytes) are necessary for blood clotting and when their numbers are very low a patient is at risk of death from catastrophic hemorrhage, TPO has potential useful application in both the diagnosis and the treatment of various hematological disorders, for example, diseases primarily due to platelet defects (see Harker et al. *Blood* 91: 4427-4433 (1998)). Ongoing clinical trials with TPO have indicated that TPO can be administered safely to patients (see Basser et al. Blood 89: 3118-3128 (1997); Fanucchi et al. *New Engl. J. Med.* 336: 404-409 (1997)). In addition, recent studies have provided a basis for the projection of efficacy of TPO therapy in the treatment of thrombocytopenia, and particularly thrombocytopenia resulting from chemotherapy, radiation therapy, or bone marrow transplantation as treatment for cancer or lymphoma. (See Harker, *Curr. Opin. Hematol.* 6: 127-134 (1999)).

The gene encoding TPO has been cloned and characterized. See Kuter et al., *Proc. Natl. Acad. Sci. USA* 91: 11104-11108 (1994); Barley et al., *Cell* 77: 1117-1124 (1994); Kaushansky et al., *Nature* 369:568-571 (1994); Wendling et al., *Nature* 369: 571-574 (1994); and Sauvage et al., *Nature* 369: 533-538 (1994). Thrombopoietin is a glycoprotein with at least two forms, with apparent molecular masses of 25 kDa and 31 kDa, with a common N-terminal amino acid; sequence. See, Baatout, *Haemostasis* 27: 1-8 (1997); Kaushansky, *New Engl. J. Med.* 339: 746-754 (1998). Thrombopoietin appears to have two distinct regions separated by a potential Arg-Arg cleavage site. The amino-terminal region is highly conserved in man and mouse, and has some homology with erythropoietin and interferon-a and interferon-b. The carboxy-terminal region shows wide species divergence.

The DNA sequences and encoded peptide sequences for human TPO receptor (TPO-R; also known as c-mpl) have been described. (See, Vigon et al. *Proc. Natl. Acad. Sci. USA* 89: 5640-5644 (1992)). TPO-R is a member of the haematopoietin growth factor receptor family, a family characterized by a common structural design of the extracellular domain, including for conserved C residues in the N-terminal portion and a WSXWS motif close to the transmembrane region. (See Bazan *Proc. Natl. Acad. Sci. USA* 87: 6934-6938 (1990)). Evidence that this receptor plays a functional role in hematopoiesis includes observations that its expression is restricted to spleen, bone marrow, or fetal liver in mice (see Souyri et al. *Cell* 63: 1137-1147 (1990)) and to megakaryocytes, platelets, and CD34$^+$ cells in humans (see Methia et al. *Blood* 82: 1395-1401 (1993)). Further evidence for TPO-R as a key regulator of megakaryopoiesis is the fact that exposure of CD34$^+$ cells to synthetic oligonucleotides antisense to TPO-R RNA significantly inhibits the appearance of megakaryocyte colonies without affecting erythroid or myeloid colony formation. Some workers postulate that the receptor functions as a homodimer, similar to the situation with the receptors for G-CSF and erythropoietin. (see Alexander et al. *EMBO J.* 14: 5569-5578 (1995)).

The slow recovery of platelet levels in patients suffering from thrombocytopenia is a serious problem, and has lent urgency to the search for a blood growth factor agonist able to accelerate platelet regeneration (see Kuter, *Seminars in Hematology*, 37: Supp 4: 41-49 (2000)).

It would be desirable to provide compounds which allow for the treatment of thrombocytopenia by acting as a TPO mimetic.

As disclosed herein it has unexpectedly been discovered that certain hydroxy-1-azo-benzene derivatives are effective as agonists of the TPO receptor, they are potent TPO mimetics.

SUMMARY OF THE INVENTION

This invention relates to compounds of Formula (I):

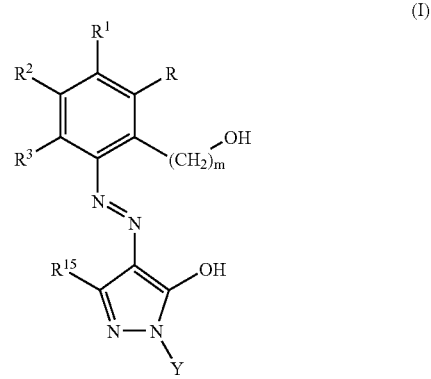

wherein:

R, $R^1$, $R^2$ and $R^3$ are each independently selected from hydrogen, $C_{1-6}$alkyl, $—(CH_2)_pOR^4$, $—C(O)OR^4$, formyl, nitro, cyano, halogen, aryl, substituted aryl, substituted alkyl, $—S(O)_nR^4$, cycloalkyl, $—NR^5R^6$, protected —OH, $—CONR^5R^6$, phosphonic acid, sulfonic acid, phosphinic acid, $—SO_2NR^5R^6$, a heterocyclic methylene substituent as represented by Formula (III),

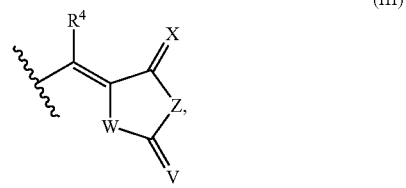

(III)

and a substituent as represented by Formula (VII),

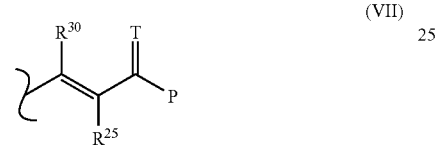

(VII)

where, p is 0-6, n is 0-2,

W and Z are each independently selected from C, O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, V and X are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen, T is absent or selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, P is selected from $OR^4$, $SR^4$, $NR^5R^6$, and $R^4$, where $R^4$ is selected from: hydrogen, alkyl, cycloalkyl, $C_1$-$C_{12}$aryl, substituted alkyl, substituted cycloalkyl and substituted $C_1$-$C_{12}$aryl, $R^{25}$ is selected from: hydrogen, alkyl, cycloalkyl, $C_1$-$C_{12}$aryl, substituted alkyl, substituted cycloalkyl and substituted $C_1$-$C_{12}$aryl, and $R^{30}$ is selected from: hydrogen, alkyl, cycloalkyl, $C_1$-$C_{12}$aryl, substituted alkyl, substituted cycloalkyl and substituted $C_1$-$C_{12}$aryl;

$R^{15}$ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is a cyclic or polycyclic, unsaturated or saturated, non-aromatic ring containing from 3 to 16 carbon atoms and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, $—C(O)OR^4$, $—C(O)NR^{10}R^{11}$, $—S(O)_2NR^{10}R^{11}$, $—S(O)_nR^4$ and protected —OH, where n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, $—C(O)OR^4$, $—S(O)_nR^4$, $—C(O)NR^4R^4$, $—S(O)_2NR^4R^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0-2;

and pharmaceutically acceptable salts, hydrates, solvates and esters thereof;

provided that at least one of R, $R^1$, $R^2$ and $R^3$ is a substituted aryl group or a heterocyclic methylene substituent as represented in Formula (III) or a substituent as represented in Formula (VII).

This invention relates to a method of treating thrombocytopenia, which comprises administering to a subject in need thereof an effective amount of a TPO mimetic compound of Formula (I).

The present invention also relates to the discovery that the compounds of Formula (I) are active as agonists of the TPO receptor.

In a further aspect of the invention there is provided novel processes and novel intermediates useful in preparing the presently invented TPO mimetic compounds.

Included in the present invention are pharmaceutical compositions comprising a pharmaceutical carrier and compounds useful in the methods of the invention.

Also included in the present invention are methods of co-administering the presently invented TPO mimetic compounds with further active ingredients.

DETAILED DESCRIPTION OF THE INVENTION

This invention relates to compounds of Formula (I) as described above.

Included among the presently invented compounds of Formula (I) are those having Formula (V):

$$\text{(V)}$$

[Structure V]

wherein:

R, $R^1$, $R^2$ and $R^3$ are each independently selected from hydrogen, $C_{1-6}$alkyl, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid, —$SO_2NR^5R^6$, a heterocyclic methylene substituent as represented by Formula (III), $$\text{(III)}$$

[Structure III]

and a substituent as represented by Formula (VII), $$\text{(VII)}$$

[Structure VII]

where, p is 0-6, n is 0-2,

W and Z are each independently selected from C, O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, V and X are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen, T is absent or selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, P is selected from $OR^4$, $SR^4$, $NR^5R^6$, and $R^4$, where $R^4$ is selected from: hydrogen, alkyl, cycloalkyl, $C_1$-$C_{12}$aryl, substituted alkyl, substituted cycloalkyl and substituted $C_1$-$C_{12}$aryl, $R^{25}$ is selected from: hydrogen, alkyl, cycloalkyl, $C_1$-$C_{12}$aryl, substituted alkyl, substituted cycloalkyl and substituted $C_1$-$C_{12}$aryl, and $R^{30}$ is selected from: hydrogen, alkyl, cycloalkyl, $C_1$-$C_{12}$aryl, substituted alkyl, substituted cycloalkyl and substituted $C_1$-$C_{12}$aryl;

$R^{15}$ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is a cyclic or polycyclic, unsaturated or saturated, non-aromatic ring containing from 4 to 15 carbon atoms and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —$C(O)OR^4$, —$C(O)NR^{10}R^{11}$, —$S(O)_2NR^{10}R^{11}$, —$S(O)_nR^4$ and protected —OH, where n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —$C(O)OR^4$, —$S(O)_nR^4$, —$C(O)NR^4R^4$, —$S(O)_2NR^4R^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0-2;

and pharmaceutically acceptable salts, hydrates, solvates and esters thereof;

provided that at least one of R, $R^1$, $R^2$ and $R^3$ is a substituted aryl group or a heterocyclic methylene substituent as represented in Formula (III) or a substituent as represented in Formula (VII).

Included among the presently invented compounds of Formula (I) are those having Formula (II):

$$\text{(II)}$$

[Structure II]

wherein:
R, $R^1$, $R^2$ and $R^3$ are each independently selected from hydrogen, $C_{1-6}$alkyl, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —H, —$CONR^5R^6$, phosphonic acid, sulfonic acid, phosphinic acid, —$SO_2NR^5R^6$, a heterocyclic methylene substituent as represented by Formula (III),

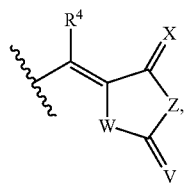

(III)

and a substituent as represented by Formula (VII),

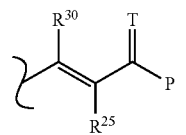

(VII)

where,
p is 0-6,
n is 0-2,
W and Z are each independently selected from C, O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl,
V and X are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl,
$R^4$ is selected from: hydrogen, alkyl, cycloalkyl, $C_1$-$C_{12}$aryl, substituted alkyl, substituted cycloalkyl and substituted $C_1$-$C_{12}$aryl,
$R^5$ and $R^6$ are each independently selected from hydrogen, alkyl, substituted alkyl, $C_{3-6}$cycloalkyl, and aryl,
or $R^5$ and $R^6$ taken together with the nitrogen to which they are attached represent a 5 to 6 member saturated ring containing up to one other heteroatom selected from oxygen and nitrogen,
T is absent or selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl,
P is selected from $OR^4$, $SR^4$, $NR^5R^6$, and $R^4$, where $R^4$ is selected from: hydrogen, alkyl, cycloalkyl, $C_1$-$C_{12}$aryl, substituted alkyl, substituted cycloalkyl and substituted $C_1$-$C_{12}$aryl,
$R^{25}$ is selected from: hydrogen, alkyl, cycloalkyl, $C_1$-$C_{12}$aryl, substituted alkyl, substituted cycloalkyl and substituted $C_1$-$C_{12}$aryl, and
$R^{30}$ is selected from: hydrogen, alkyl, cycloalkyl, $C_1$-$C_{12}$aryl, substituted alkyl, substituted cycloalkyl and substituted $C_1$-$C_{12}$aryl;
$R^{15}$ is selected from the group consisting of alkyl, $C_1$-$C_{12}$aryl, hydroxy, alkoxy, substituted alkyl, substituted $C_1$-$C_{12}$aryl and halogen;
m is 0-6; and Y is a cyclic or polycyclic, unsaturated or saturated, non-aromatic ring containing from 5 to 14 carbon atoms and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —$C(O)OR^4$, —$C(O)NR^{10}R^{11}$, —$S(O)_2NR^{10}R^{11}$, —$S(O)_nR^4$ and protected —OH,
where n is 0-2,
$R^4$ is hydrogen, alkyl, cycloalkyl, $C_1$-$C_{12}$aryl, substituted alkyl, substituted cycloalkyl and substituted $C_1$-$C_{12}$aryl, and
$R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —$C(O)OR^4$, —$S(O)_nR^4$, —$C(O)NR^4R^4$, —$S(O)_2NR^4R^4$, nitro, cyano, cycloalkyl, substituted cycloalkyl, halogen, aryl, substituted aryl and protected —OH,
or $R^{10}$ and $R^{11}$ taken together with the nitrogen to which they are attached represent a 5 to 6 member saturated ring containing up to one other heteroatom selected from oxygen and nitrogen,
where $R^4$ is as described above and n is 0-2;
and pharmaceutically acceptable salts, hydrates, solvates and esters thereof;
provided that at least one of R, $R^1$, $R^2$ and $R^3$ is a substituted aryl group or a heterocyclic methylene substituent as represented in Formula (III) or a substituent as represented in Formula (VII).

Included among the presently invented compounds of Formula (II) are compounds in which $R^{15}$ is not alkoxy.

Included among the presently invented compounds of Formula (II) are those having Formula (VI):

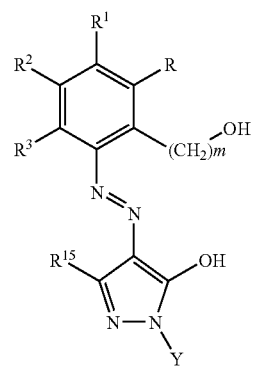

(VI)

wherein:
R, $R^1$, $R^2$ and $R^3$ are each independently selected from hydrogen, $C_{1-6}$alkyl, $C_{1-6}$alkoxy, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid, —$SO_2NR^5R^6$, a heterocyclic methylene substituent as represented by Formula (III),

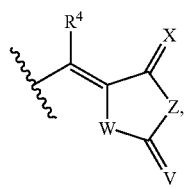

(III)

and a substituent as represented by Formula (VII),

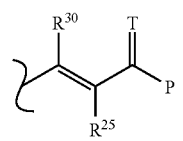

(VII)

where, n is 0-2,

W and Z are each independently selected from C, O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, V and X are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen, T is absent or selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, P is selected from $OR^4$, $SR^4$, $NR^5R^6$, and $R^4$, where $R^4$ is selected from: hydrogen, alkyl, cycloalkyl, $C_1$-$C_{12}$aryl, substituted alkyl, substituted cycloalkyl and substituted $C_1$-$C_{12}$aryl, $R^{25}$ is selected from: hydrogen, alkyl, cycloalkyl, $C_1$-$C_{12}$aryl, substituted alkyl, substituted cycloalkyl and substituted $C_1$-$C_{12}$aryl, and $R^{30}$ is selected from: hydrogen, alkyl, cycloalkyl, $C_1$-$C_{12}$aryl, substituted alkyl, substituted cycloalkyl and substituted $C_1$-$C_{12}$aryl;

$R^{15}$ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is a cyclic or polycyclic, unsaturated or saturated, non-aromatic ring containing from 5 to 12 carbon atoms and optionally substituted with one or more substituents selected from the group consisting of: alkyl, substituted alkyl, $C_1$-$C_{12}$aryl, substituted cycloalkyl, substituted $C_1$-$C_{12}$aryl, hydroxy, aryloxy, alkoxy, cycloalkyl, nitro, cyano, halogen and protected —OH;

and pharmaceutically acceptable salts, hydrates, solvates and esters thereof;

provided that at least one of R, $R^1$, $R^2$ and $R^3$ is a substituted aryl group or a heterocyclic methylene substituent as represented in Formula (III) or a substituent as represented in Formula (VII).

Also included among the presently invented compounds of Formula (II) are compounds of Formula (VI) in which $R^{15}$ is not alkoxy.

Included among the presently invented Formula VI compounds are those in which:

R is a substituted aryl; and $R^1$ is hydrogen;

R is hydrogen; and $R^1$ is a substituted aryl;

R is a hydrogen; and $R^1$ is a substituent as represented in Formula (III); or

R is a hydrogen; and $R^1$ is a substituent as represented in Formula (VII);

and in each of the above cases:

$R^2$ and $R^3$ are each independently selected from hydrogen, $C_{1-6}$alkyl, $C_{1-6}$alkoxy, nitro, cyano, halogen, aryl, substituted aryl, substituted alkyl, cycloalkyl, phosphonic acid, phosphinic acid and sulfonic acid;

$R^{15}$ is selected from the group consisting of alkyl, substituted alkyl, $C_1$-$C_{12}$aryl, alkoxy and halogen;

m is 0-4; and

Y is selected from,
cyclohexyl, cyclopentyl and cycloheptyl, where the cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;

and pharmaceutically acceptable salts, hydrates, solvates and esters thereof.

Preferred among the presently invented Formula VI compounds are those in which:

R is a substituted $C_1$-$C_{12}$aryl; and $R^1$ is hydrogen;

R is a hydrogen; and $R^1$ is a substituent as represented in Formula (III); or

R is a hydrogen; and $R^1$ is a substituent as represented in Formula (VII);

and in each of the above cases:

$R^2$ and $R^3$ are each independently selected from hydrogen, $C_{1-6}$alkyl, $C_{1-6}$alkoxy, nitro, cyano, halogen, substituted alkyl and cycloalkyl;

$R^{15}$ is selected from the group consisting of alkyl, substituted alkyl, $C_1$-$C_{12}$aryl, alkoxy and halogen;

m is 0-2; and

Y is selected from,
cyclohexyl, cyclopentyl and cycloheptyl, where the cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;

and additionally, when R is a hydrogen; and $R^1$ is a substituent as represented in Formula (VII):
$R^{25}$ and $R^{30}$ are each selected from: hydrogen, $C_{1-6}$alkyl, $C_{1-6}$alkoxy, substituted $C_{1-6}$alkyl and cycloalkyl;

and additionally, when R is a hydrogen; and $R^1$ is a substituent as represented in Formula (VII); and when R is a hydrogen; and $R^1$ is a substituent as represented in Formula (III);
$R^4$ is selected from: hydrogen, $C_{1-6}$alkyl, $C_{1-6}$alkoxy, substituted $C_{1-6}$alkyl and cycloalkyl;

and pharmaceutically acceptable salts, hydrates, solvates and esters thereof.

Preferred among the presently invented Formula VI compounds are those in which, either:
R is a substituted phenyl ring and $R^1$ is hydrogen; or
R is a hydrogen; and $R^1$ is a substituent as represented in Formula (III); and in either of the above cases:
$R^2$ and $R^3$ are each independently selected from hydrogen, $C_{1-6}$alkyl, substituted alkyl and halogen;
$R^{15}$ is selected from the group consisting of $C_{1-4}$alkyl, $C_{1-4}$alkoxy, $C_1$-$C_{12}$aryl and halogen;
m is 0; and
Y is selected from,
cyclohexyl, cyclopentyl and cycloheptyl, where cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;

and additionally, when R is a hydrogen; and $R^1$ is a substituent as represented in Formula (III);
$R^4$ is selected from: hydrogen, $C_{1-6}$alkyl, $C_{1-6}$alkoxy, substituted $C_{1-6}$alkyl and cycloalkyl;
and pharmaceutically acceptable salts, hydrates, solvates and esters thereof.

Preferred among the presently invented compounds are:
3'-(1-Cyclohexyl-5-hydroxy-3-methyl-1H-pyrazol-4-ylazo)-2'-hydroxy-biphenyl-3-carboxylic acid;
3'-[1-(4-tert-Butyl-cyclohexyl)-5-hydroxy-3-methyl-1H-pyrazol-4-ylazo]-2'-hydroxy-biphenyl-3- carboxylic acid;
3'-[1-(3,4-Dimethyl-cyclohexyl)-5-hydroxy-3-methyl-1H-pyrazol-4-ylazo]-2'-hydroxy-biphenyl-3- carboxylic acid;
3'-[1-(3,4-Dichloro-cyclohexyl)-5-hydroxy-3-methyl-1H-pyrazol-4-ylazo]-2'-hydroxy-biphenyl-3- carboxylic acid;
5-[4-(1-Cyclohexyl-5-hydroxy-3-methyl-1H-pyrazol-4-ylazo)-3-hydroxy-benzylidene ]-thiazolidine-2,4-dione;
5-{4-[1-(4-tert-Butyl-cyclohexyl)-5-hydroxy-3-methyl-1H-pyrazol-4-ylazo]-3-hydroxy-benzylidene}-thiazolidine-2,4-dione;
5-{4-[1-(3,4-Dimethyl-cyclohexyl)-5-hydroxy-3-methyl-1H-pyrazol-4-ylazo]-3-hydroxy-benzylidene}-thiazolidine-2,4-dione;
5-{4-[1-(3,4-Dichloro-cyclohexyl)-5-hydroxy-3-methyl-1H-pyrazol-4-ylazo]-3-hydroxy-benzylidene}-thiazolidine-2,4-dione;
(E)-3-{4-[1-(4-tert-butylcyclohexyl)-3-methyl-5-oxo-4,5-dihydro-1H-pyrazol-4-ylazo]-3-hydroxyphenyl}-2-methylacrylic acid;
(E)-3-(4-{N'-3-Ethylcyclopentyl)-3-methyl-5-oxo-1,5-dihydropyrazol-4-ylidene]-hydrazino}-3-hydrophenyl-2-methylacrylic acid; and
(E)-3-[4-(N'-{1-[3-(1,1-Dimethylpropyl)-cyclopentyl]-3-methyl-5-oxo-1,5-dihydropyrazol-4-ylidene}-hydrazino)-3-hydroxyphenyl]-2- methylacrylic acid;

and pharmaceutically acceptable salts, hydrates, solvates and esters thereof.

Preferred among the presently invented compounds are:
3'-(1-Cyclohexyl-5-hydroxy-3-methyl-1H-pyrazol-4-ylazo)-2'-hydroxy-biphenyl-3- carboxylic acid;
5-{4-[1-(4-tert-Butyl-cyclohexyl)-5-hydroxy-3-methyl-1H-pyrazol-4-ylazo]-3-hydroxy-benzylidene}-thiazolidine-2,4-dione;
(E)-3-{4-[1-(4-tert-butylcyclohexyl)-3-methyl-5-oxo-4,5-dihydro-1H-pyrazol-4-ylazo]-3-hydroxyphenyl}-2-methylacrylic acid;
(E)-3-{4-(N'-3-Ethylcyclopentyl)-3-methyl-5-oxo-1,5-dihydropyrazol-4-ylidene]-hydrazino}-3-hydrophenyl-2-methylacrylic acid; and
(E)-3-[4-(N'-{1-[3-(1,1-Dimethylpropyl)-cyclopentyl]-3-methyl-5-oxo-1,5-dihydropyrazol-4-ylidene}-hydrazino)-3-hydroxyphenyl]-2- methylacrylic acid;

and pharmaceutically acceptable salts, hydrates, solvates and esters thereof.

Among the compounds of Formula (I) are compounds that are generally described, but not specifically prepared, in International Application No. PCT/US01/16863, having an International filing date of May 24, 2001; International Publication Number WO 01/89457 and an International Publication date of Nov. 29, 2001. Specifically, compounds of the present invention in which Y is a nonaromatic, unsaturated or saturated, cyclic or polycyclic $C_3$-$C_{12}$, and in which R, $R^1$, $R^2$ or $R^3$ are other than a substituent of Formula (VII),

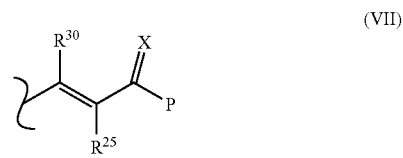

(VII)

are generically but not specifically claimed in International Application No. PCT/US01/16863. The present invention, in part, relates to unexpected enhanced properties of the compounds described herein. Specifically, compounds of the present invention were surprisingly found to have a preferred solubility profile in comparison to the compounds prepared in International Application No. PCT/US01/16863. Specifically, compounds of the present invention were surprisingly found to have a preferred toxicity profile in comparison to the compounds prepared in International Application No. PCT/US01/16863.

Compounds of Formula (I) are included in the pharmaceutical compositions of the invention and used in the methods of the invention.

By the term "protected hydroxy" or "protected —OH" as used herein, is meant the alcoholic or carboxylic-OH groups which can be protected by conventional blocking groups in the art such as described in "Protective Groups In Organic Synthesis" by Theodora W. Greene, Wiley-Interscience, 1981, New York. Compounds containing protected hydroxy groups may also be useful as intermediates in the preparation of the pharmaceutically active compounds of the invention.

By the term "aryl" as used herein, unless otherwise defined, is meant a cyclic or polycyclic aromatic ring containing from 1 to 14 carbon atoms and optionally containing from one to five heteroatoms, provided that when the number of carbon atoms is 1 the aromatic ring contains at least four heteroatoms, when the number of carbon atoms is 2 the aromatic ring contains at least three heteroatoms, when the number of carbons is 3 the aromatic ring contains at least two heteroatoms and when the number of carbon atoms is 4 the aromatic ring contains at least one heteroatom.

By the term "$C_1$-$C_{12}$aryl" as used herein, unless otherwise defined, is meant phenyl, naphthalene, 3,4-methylenedioxyphenyl, pyridine, biphenyl, quinoline, pyrimidine, quinazoline, thiophene, furan, pyrrole, pyrazole, imidazole and tetrazole.

When referring to compounds of Formula (I) and (II), the term "substituted" as used herein, unless otherwise defined, is meant that the subject chemical moiety has one or more substituents selected from the group consisting of: —$CO_2R^{20}$, aryl, —$C(O)NHS(O)_2R^{20}$, —$NHS(O)_2R^{20}$, hydroxyalkyl, alkoxy, —C(O)NR²¹R²², acyloxy, alkyl, amino, N-acylamino, hydroxy, —(CH₂)$_g$C(O)OR⁸, —S(O)$_n$R⁸, nitro, tetrazole, cyano, oxo, halogen, trifluoromethyl, protected —OH, a heterocyclic methylene substituent as represented by Formula (III),

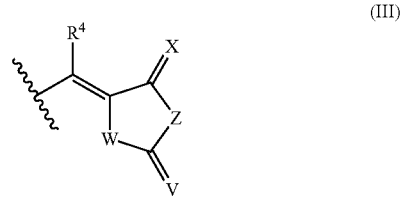

and a substituent as represented by Formula (VII),

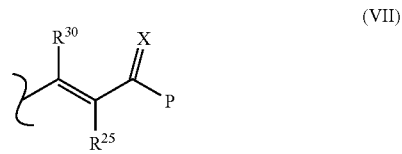

where g is 0-6; R⁸ is hydrogen or alkyl; R²⁰ is selected form hydrogen, C₁-C₄alkyl, aryl and trifluoromethyl; R²¹ and R²² are independently selected form hydrogen, C₁-C₄alkyl, aryl and trifluoromethyl; W and Z are each independently selected from C, O, S, and NR¹⁶, where R¹⁶ is selected from: hydrogen, alkyl, cycloalkyl, C₁-C₁₂aryl, substituted alkyl, substituted cycloalkyl and substituted C₁-C₁₂aryl; V and X are each independently selected from O, S, and NR¹⁶, where R¹⁶ is selected from: hydrogen, alkyl, cycloalkyl, C₁-C₁₂aryl, substituted alkyl, substituted cycloalkyl and substituted C₁-C₁₂aryl; R²⁵ and R³⁰ are independently selected from: hydrogen, alkyl, cycloalkyl, C₁-C₁₂aryl, substituted alkyl, substituted cycloalkyl and substituted C₁-C₁₂aryl; and n is 0-2.

When referring to compounds of Formula (V) and (VI), the term "substituted" as used herein, unless otherwise defined, is meant that the subject chemical moiety has one or more substituents selected from the group consisting of: —CO₂R²⁰, aryl, —C(O)NHS(O)₂R²⁰, —NHS(O)₂R²⁰, hydroxyalkyl, alkoxy, —C(O)NR²¹R²², acyloxy, alkyl, amino, N-acylamino, hydroxy, —(CH₂)$_g$C(O)OR⁸, —S(O)$_n$R⁸, nitro, tetrazole, cyano, oxo, halogen, trifluoromethyl and protected —OH, where g is 0-6, R⁸ is hydrogen or alkyl, R²⁰ is selected form hydrogen, C₁-C₄alkyl, aryl and trifluoromethyl, and R²¹ and R²² are independently selected form hydrogen, C₁-C₄alkyl, aryl and trifluoromethyl, and n is 0-2.

By the term "alkoxy" as used herein is meant —Oalkyl where alkyl is as described herein including —OCH₃ and —OC(CH₃)₂CH₃.

The term "cycloalkyl" as used herein unless otherwise defined, is meant a nonaromatic, unsaturated or saturated, cyclic or polycyclic C₃-C₁₂.

Examples of cycloalkyl and substituted cycloalkyl substituents as used herein include: cyclohexyl, 4-hydroxy-cyclohexyl, 2-ethylcyclohexyl, propyl 4-methoxycyclohexyl, 4-methoxycyclohexyl, 4-carboxycyclohexyl, cyclopropyl and cyclopentyl.

By the term "acyloxy" as used herein is meant —OC(O) alkyl where alkyl is as described herein. Examples of acyloxy substituents as used herein include: —OC(O)CH₃, —OC(O)CH(CH₃)₂ and —OC(O)(CH₂)₃CH₃.

By the term "N-acylamino" as used herein is meant —N(H)C(O)alkyl, where alkyl is as described herein. Examples of N-acylamino substituents as used herein include: —N(H)C(O)CH₃, —N(H)C(O)CH(CH₃)₂ and —N(H)C(O)(CH₂)₃CH₃.

By the term "aryloxy" as used herein is meant —Oaryl where aryl is phenyl, naphthyl, 3,4-methylenedioxyphenyl, pyridyl or biphenyl optionally substituted with one or more substituents selected from the group consisting of: alkyl, hydroxyalkyl, alkoxy, trifuloromethyl, acyloxy, amino, N-acylamino, hydroxy, —(CH₂)$_g$C(O)OR⁸, —S(O)$_n$R⁸, nitro, cyano, halogen and protected —OH, where g is 0-6, R⁸ is hydrogen or alkyl, and n is 0-2. Examples of aryloxy substituents as used herein include: phenoxy, 4-fluorophenyloxy and biphenyloxy.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein is meant a linear or branched, saturated or unsaturated hydrocarbon chain, and unless otherwise defined, the carbon chain will contain from 1 to 12 carbon atoms. Examples of alkyl substituents as used herein include: —CH₃, —CH₂—CH₃, —CH₂—CH₂—CH₃, —CH(CH₃)₂, —C(CH₃)₃, —(CH₂)₃—CH₃, —CH₂—CH(CH₃)₂, —CH(CH₃)—CH₂—CH₃, —CH=CH₂, and —C.C—CH₃.

By the term "treating" and derivatives thereof as used herein, is meant prophylatic and therapeutic therapy.

All publications, including but not limited to patents and patent applications, cited in this specification are herein incorporated by reference as though fully set forth.

Compounds of Formula (I) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The novel compounds of Formulas I and II are prepared by methods analogous to those shown in Schemes I to VI below. All of the starting materials are commercially available or are readily made from commercially available starting materials by those of skill in the art.

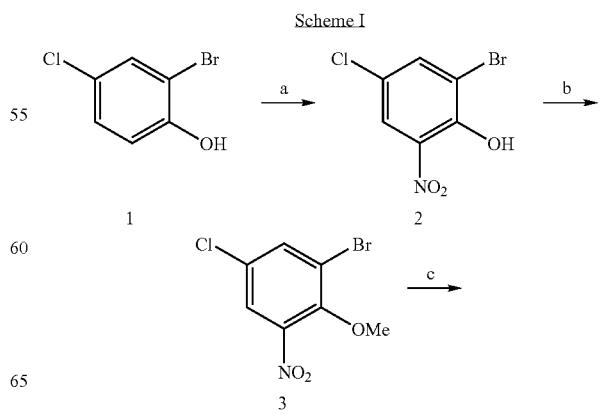

Scheme I

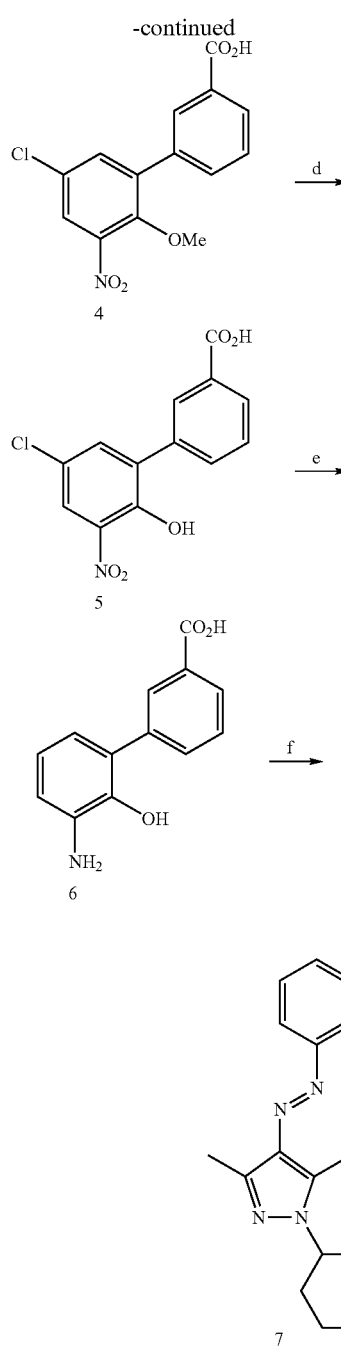

a NaNO₂, H₂SO₄;
b MeI, K₂CO₃, acetone;
c 3-carboxyphenylboronic acid, Pd(PPh₃)₄, Na₂CO₃, dioxane, H₂O;
d 48% aq. HBr, AcOH;
e H₂, 10% Pd/C;
f i - NaNO₂, HCl, EtOH/H₂O,
  ii - 2-cyclohexyl-5-methyl-2H-pyrazol-3-ol, NaHCO₃.

texts such as March, "Advanced Organic Chemistry: reactions, mechanisms, and structure," Wiley, N.Y. (1992). The phenol is then protected by reaction with an alkylating agent such as benzyl bromide or preferably methyl iodide in the presence of a base such as sodium hydride or potassium carbonate in a suitable solvent such as dimethylformamide, tetrahydrofuran or acetone to give protected nitrophenol, 3-Scheme I. Subsequent reaction with a substituted arylboronic acid, such as 3-carboxyphenylboronic acid or 4-carboxyphenylboronic acid, in the presence of a catalyst, preferably tetrakistriphenylphosphino palladium and a base such as sodium carbonate ot triethylamine in a suitable solvent such as aqueous 1,4-dioxane or dimethylformamide afforded substituted aryl compound, 4-Scheme I. Removal of the protecting group is accomplished using an protic or Lewis acid; such as concentrated hydrobromic acid, boron tribromide or trimethylsilyl iodide to affored the phenol 5-Scheme I. Reduction of the nitro group by catalytic hydrogenation or mediated by a reducing metal such as iron of tin dichloride in a suitable solvent such as ethanol, acetic acid; or water gives the aniline 6-Scheme I. This is diazotized by reaction with sodium nitrite and an appropriate acid, such as nitric acid, sulfuric acid or, preferably, hydrochloric acid, in an appropriate aqueous solvent, such as water or, preferably, an ethanol-water mixture to produce a diazonium species which is directly converted to a compound of Formula (I) (7-Scheme I) by reacting with an appropriate pyrazole in the presence of a base, preferably sodium hydrogen carbonate, or an acid, preferably hydrochloric acid.

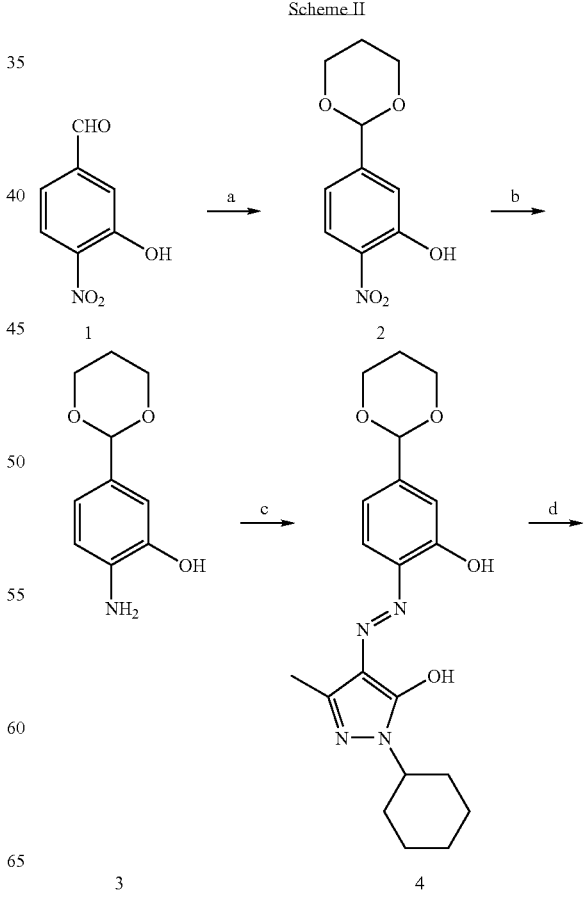

Scheme II

Compounds of Formula I can be prepared in a manner analogous to those shown in Scheme I. An appropriate bromophenol, such as 1-Scheme I, reacted with NaNO2 in sulfuric acid to give the corresponding nitrophenol, 2-Scheme I. Alternatively, the nitration can be carried out using nitric acid. Other alternative methods exist and are known to those skilled in the art for carrying out this transformation. A compilation of these methods can be found in standard organic synthesis -continued

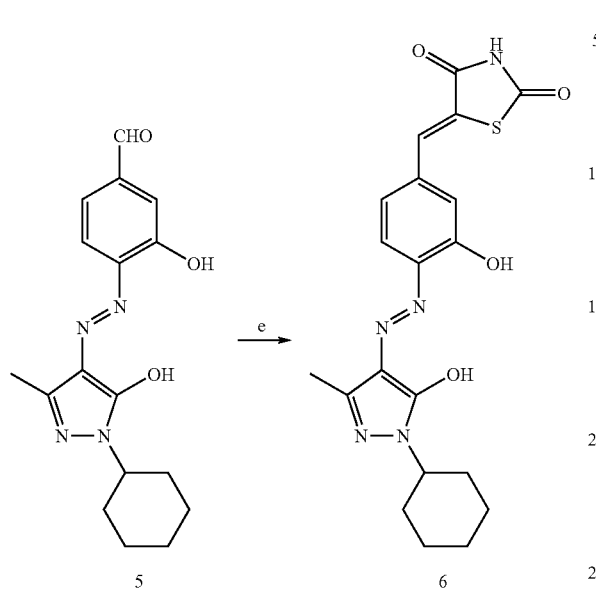

a propanediol, p-TsOH, toluene, reflux;
b PtO$_2$ H$_2$, EtOAc;
c i - NaNO$_2$, HCl, EtOH/H$_2$O,
 ii - 2-cyclohexyl-5-2H-pyrazol-3-ol, NaHCO$_3$;
d HCl, MeOH/H2O;
e thiazolidinedione, piperidine, EtOH, reflux.

Alternatively, the compounds for Formula (I) can be prepared as shown in Scheme II. The aldehyde function of an appropriate nitro aldehyde, such as 1-Scheme II, is protected by reaction with 1,3-propanediol to give the corresponding cyclic acetal, 2-Scheme II. Many different protecting groups are available to one skilled in the art and can be used here as long as they do not interefere with the processes listed in Scheme II. A compilation of these groups can be found in Greene and Wuts, "Protective Groups in Organic Synthesis. 2nd Ed., Wiley, N.Y. (1991). The nitro group is then reduced using either a reducing metal or catalytic hydrogenation with an appropriate catalyst such as platinum oxide to give the corresponding anilin, 3-Scheme II. Diazotization with sodium nitrite and an appropriate acid, such as nitric acid, sulfuric acid or, preferably, hydrochloric acid, in an appropriate aqueous solvent, such as an ethanol-water mixture gives the diazonium species which is directly coupled with an appropriate pyrazolone to give a product such as 4-Scheme II. The protected aldehyde is unmasked under acidic aqueous conditions to give the parent aldehyde, such as 5-Scheme II. A Knoevenagel condensation (Knoevenagel, Chemische Berichte 29: 172 (1896))with an active methylene compound furnishes a compound of Formula (I), such as 6-Scheme II.

Scheme III

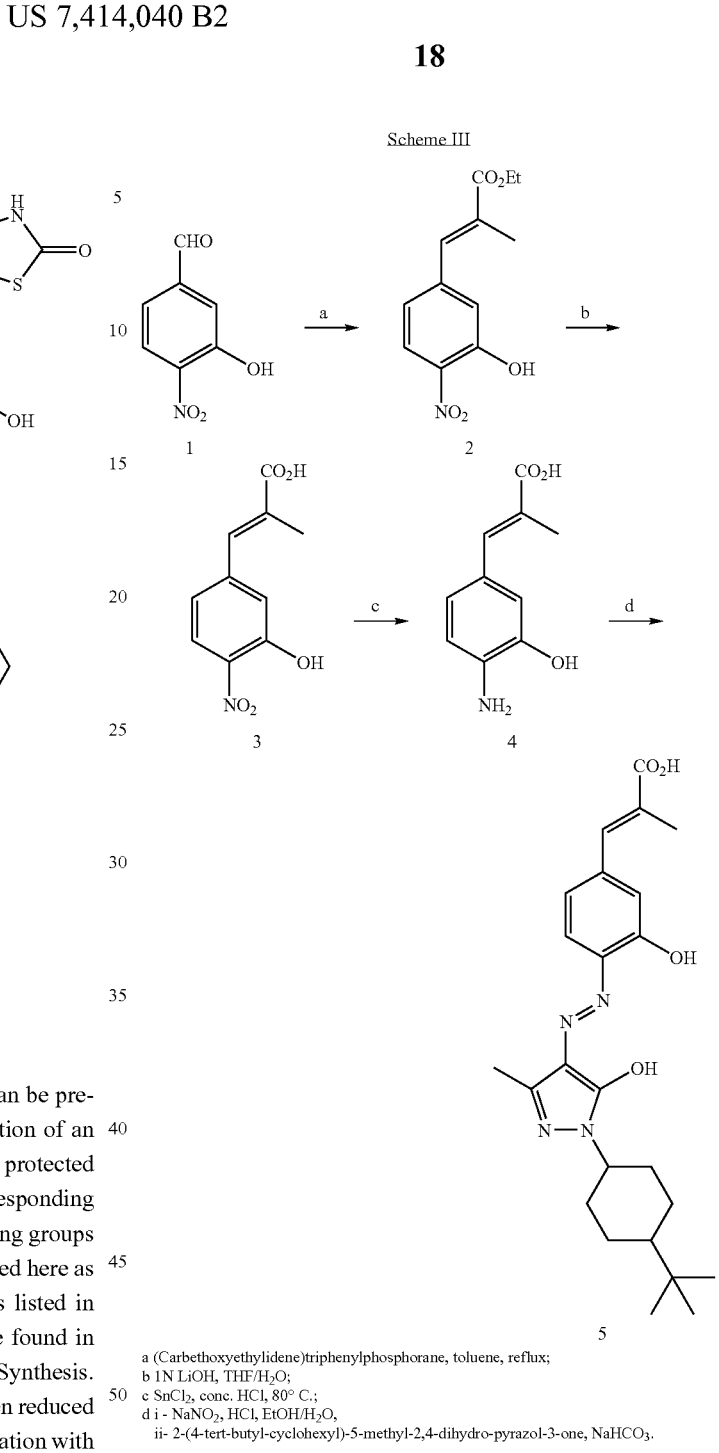

a (Carbethoxyethylidene)triphenylphosphorane, toluene, reflux;
b 1N LiOH, THF/H$_2$O;
c SnCl$_2$, conc. HCl, 80° C.;
d i - NaNO2, HCl, EtOH/H$_2$O,
 ii- 2-(4-tert-butyl-cyclohexyl)-5-methyl-2,4-dihydro-pyrazol-3-one, NaHCO$_3$.

Alternatively, the compounds for Formula (I) can also be prepared as shown in Scheme III. Olefination of an appropriate aldehyde, such as 1-Scheme III, using a Horner-Wadsworth-Emmons reaction, or preferably, a salt free Wittig reaction with an appropriate phophorane, such as (carbethoxyethylidene)triphenylphosphorane gives the corresponding olefin, 2-Scheme III. Saponification of the ester under acidic, or preferably, basic conditions using an aqeuous base, such as lithium hydroxide in THF-water, gives the corresponding acid, 3-Scheme III. The nitro group is then reduced using either catalytic hydrogenation or mediated by a reducing metal such as iron or tin dichloride in a suitable solvent, such as acetic acid or hydrochloric acid to give the corresponding aniline, 4-Scheme III. Diazotization with sodium nitrite and an appropriate acid, such as nitric acid, sulfuric acid or, preferably, hydrochloric acid, in an appropriate aqueous solvent, such as an ethanol-water mixture gives the diazonium species which is directly coupled with an appropriate pyrazolone to give a compound of Formula (I), such as 5-Scheme III.

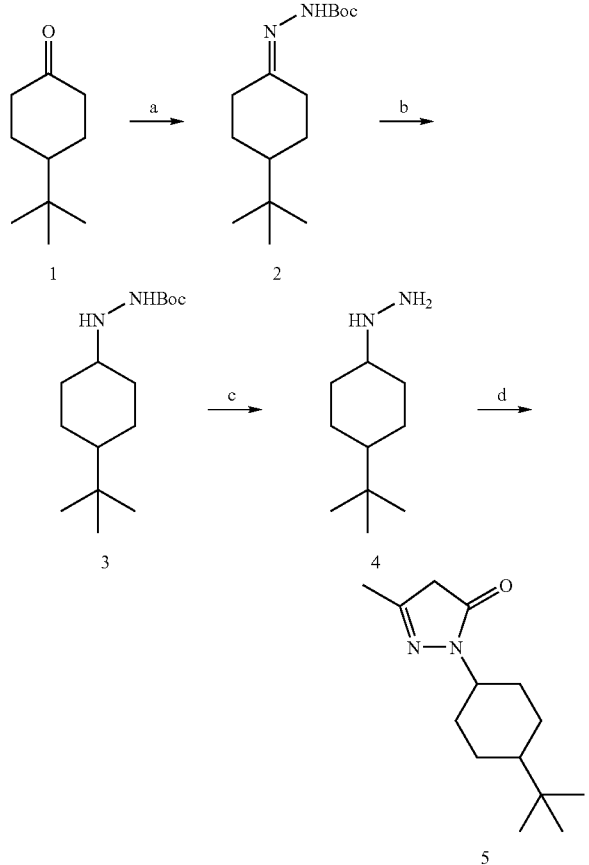

a t-Butyl carbazate, CH₂Cl₂;
b H₂, 50 psi, 10% Pd/C, THF;
c 4N HCl/dioxane;
d methyl acetoacetate, glacial acetic acid, 100° C.

Scheme IV outlines the formation of pyrazoles used in Schemes I-III. A ketone, such as 1-Scheme IV, is reacted with an appropriate carbazate, such as t-butyl carbazate, in an appropriate solvent, such as methylene chloride, to give the corresponding hydrazone, such as 2-Scheme IV. Reduction of the hydrazone by catalytic hydrogenation using an appropriate catalyst, such as palladium on carbon, in an appropriate solvent, such as THF, give a protected hydrazine, such as 3-Scheme IV. Removal of the protecting group under acidic conditions followed by cyclocondensation with an appropriate keto ester, such as methyl acetoacetate, in an appropriate solvent, such as glacial acetic acid gives the corresponding pyrazole, such as 5-Scheme IV.

In preparing the presently invented compounds of Formula (I), the following novel intermediates are prepared:

2-Cyclohexyl-5-methyl-2,4-dihydro-pyrazol-3-one;
2-(4-tert-Butyl-cyclohexyl)-5-methyl-2,4-dihydro-pyrazol-3-one;
5-(3-Hydroxy-4-nitro-benzylidene)-thiazolidine-2,4-dione;
5-(4-Amino-3-hydroxy-benzylidene)-thiazolidine-2,4-dione;
(E)-3-(4-amino-3-hydroxy-phenyl)-2-methyl-acrylic acid ethyl ester hydrochoride;
2-(3-ethylcyclopentyl)-5-methyl-2,4-dihydroxyprazol-3-one;
2-[3-(1,1-dimethylpropyl)-cyclopentyl]-5-methyl-2,4-dihydroxypyrazol-3-one;
(E)-3-(3-Hydroxy-4-nitrophenyl)-2-methylacrylic acid ethyl ester;
(E)-3-(4-Amino-3-hydroxy-phenyl)-2-methyl-acrylic acid ethyl ester hydrochloride;
3-Ethylcyclopentylhydrazine trifluoroacetate; and
3-(1,1-Dimethylpropyl)-cyclopentylhydrazine trifluoroacetate.

The treatment of thrombocytopenia, as described herein, is accomplished by increasing the production of platelets.

By the term "co-administering" and derivatives thereof as used herein is meant either simultaneous administration or any manner of separate sequential administration of a TPO mimetic compound, as described herein, and a further active ingredient or ingredients, known to treat thrombocytopenia, including chemotherapy-induced thrombocytopenia and bone marrow transplantation and other conditions with depressed platelet production. The term further active ingredient or ingredients, as used herein, includes any compound or therapeutic agent known to or that demonstrates advantageous properties when administered with TPO or a TPO mimetic. Preferably, if the administration is not simultaneous, the compounds are administered in a close time proximity to each other. Furthermore, it does not matter if the compounds are administered in the same dosage form, e.g. one compound may be administered topically and another compound may be administered orally.

Examples of a further active ingredient or ingredients for use in combination with the presently invented TPO mimetic compounds include but are not limited to: chemoprotective or myeloprotective agents such as G-CSF, BB10010 (Clemons et al., *Breast Cancer Res. Treatment*, 1999, 57, 127), amifostine (Ethyol) (Fetscher et al., *Current Opinion in Hemat.*, 2000, 7, 255-60), SCF, IL-11, MCP-4, IL-1-beta, AcSDKP (Gaudron et al., *Stem Cells*, 1999, 17, 100-6), TNF-a, TGF-b, MIP-1a (Egger et al., *Bone Marrow Transpl.*, 1998, 22 (Suppl. 2), 34-35), and other molecules identified as having anti-apoptotic, survival or proliferative properties.

Tpo has been demonstrated to act as a mobilizer of stem cells into the peripheral blood (Neumann T. A. et al., *Cytokines, Cell. & Mol. Ther.*, 2000, 6,47-56). This activity can synergize with stem cell mobilizers such as G-CSF (Somolo et al., *Blood*, 1999, 93, 2798-2806). The TPO mimetic compounds of the present invention are thus useful in increasing the numbers of stem cells in circulation in donors prior to leukapheresis for hematopoietic stem-cell transplantation in patients receiving myelo-ablative chemotherapy.

Likewise, TPO stimulates growth of myeloid cells, particularly those of granulocyte/macrophage lineage (Holly et al., U.S. Pat. No. 5,989,537). Granulocyte/macrophage progenitors are cells of the myeloid lineage that mature as neutrophils, monocytes, basophils and eosinophils. The compounds described in the present invention have thus therapeutic utility in stimulating the poliferation of neutrophils in patients with neutropenic conditions.

Additional examples of a further active ingredient or ingredients for use in combination with the presently invented TPO mimetic compounds include but are not limited to: stem cell, megakaryocyte, neutrophil mobilizers such as chemotherapeutic agents (i.e., cytoxan, etoposide, cisplatin, Ballestrero A. et al., *Oncology*, 2000, 59, 7-13), chemokines, IL-8, Grobeta (King, A. G. et al. *J. Immun.*, 2000, 164, 3774-82), receptor agonist or antagonist antibodies, small molecule cytokine or receptor agonists or antagonists, SCF, Flt3 ligand, adhesion molecule inhibitors or antibodies such as: anti-VLA-4 (Kikuta T. et al., *Exp. Hemat.*, 2000, 28, 311-7) or anti-CD44 (Vermeulen M. et al., *Blood*, 1998, 92, 894-900), cytokine/chemokine/interleukin or receptor agonist or antagonist antibodies, MCP-4 (Berkhout T A., et al., *J. Biol. Chem.*, 1997, 272, 16404-16413; Uguccioni M. et al., *J. Exp. Med.*, 1996, 183, 2379-2384).

Because the pharmaceutically active compounds of the present invention are active as TPO mimetics they exhibit therapeutic utility in treating thrombocytopenia and other conditions with depressed platelet production.

By the term "thrombocytopenia" and derivatives thereof as used herein is to be broadly interpreted as any decrease in the number of blood platelets below what is considered normal or desired for a healthy individual. Thrombocytopenia is known to have many causative factors, including but not limited to, radiation therapy, chemotherapy, immune therapy, immune thrombocytopenic purpura (ITP, Bussel J. B., *Seminars in Hematology*, 2000, 37, Suppl 1, 1-49), myelodysplastic syndrom (MDS), aplastic anemia, AML, CML, viral infections (including, but not limited to; HIV, hepatitis C, parvovirus) liver disease, myeloablation, bone marrow transplant, stem cell transplant, peripheral blood stem cell transplant, progenitor cell defect, polymorphisms in stem cells and progenitor cells, defects in Tpo, neutropenia (Sawai, N. *J. Leukocyte Biol.*, 2000, 68, 137-43), dendritic cell mobilization (Kuter D. J. *Seminars in Hematology*, 2000, 37, Suppl 4, 41-49), proliferation, activation or differentiation. The pharmaceutically active compounds of this invention are useful in treating thrombocytopenia regardless of the factor or factors causing the condition. The pharmaceutically active compounds of this invention are also useful in treating thrombocytopenia when the causative factor or factors of the condition are unknown or have yet to be identified.

Prophylactic use of the compounds of this invention is contemplated whenever a decrease in blood or blood platelets is anticipated. Prophylactic use of the compounds of this invention results in a build up of platelets or a commencement of platelet production prior to an anticipated loss of blood or blood platelets. Prophylactic uses of the compounds of this invention includes but is not limited to transplant surgery, surgery, anesthesia prior to child birth and gut protection.

Human dendritic cells have been shown to express the TPO receptor (Kumamoto et al., *Br. J. Haem*, 1999, 105, 1025-1033) and TPO is a potent mobilizer of dendritic cells. The TPO mimetic compounds of the current invention are also useful as a vaccine adjuvant in that they increase the activity and mobility of dendritic cells. The pharmaceutically active compounds of this invention are useful as an immunological adjuvant, given in combination with an orally, transdermally or subcutaneously delivered vaccine and/or immunomodulator, by increasing the activity and mobility of dendritic cells.

Tpo is known to have various effects including anti-apotoic/survival effects on megakaryocytes, platelets and stem cells, and proliferative effects on stem cells and megakaryocytic cells (Kuter D. J. Seminars in Hematology, 2000, 37, 41-9). These Tpo activities effectively increase the number of stem and progenitor cells so that there is synergistic effects when Tpo is used in conjunction with other cytokines that induce differentiation.

The TPO mimetic compounds of the current invention are also useful in acting on cells for survival or proliferation in conjunction with other agents known to act on cells for survival or proliferation. Such other agents include but are not limited to: G-CSF, GM-CSF, TPO, M-CSF, EPO, Gro-beta, IL-11, SCF, FLT3 ligand, LIF, IL-3, IL-6, IL-1, Progenipoietin, NESP, SD-01, or IL-5 or a biologically active derivative of any of the aforementioned agents, KT6352 (Shiotsu Y. et al., *Exp. Hemat.* 1998, 26, 1195-1201), uteroferrin (Laurenz J C., et al. *Comp. Biochem. & Phys., Part A. Physiology.*, 1997, 116, 369-77), FK23 (Hasegawa T., et al. *Int. J. Immunopharm.*, 1996, 18 103-112) and other molecules identified as having anti-apoptotic, survival or proliferative properties for stem cells, progenitor cells, or other cells expressing Tpo Receptors.

In determining potency as TPO mimetics, the following assays were employed:

Proliferation Assay

Compounds of the present invention were tested for potency as mimetics of TPO in an in vitro proliferation assay using the murine BaF3 cell line transfected with human Tpo-R. Survival and growth is dependent on the presence of TPO.

Compounds of this invention were active in an in vitro proliferation assay using the human UT7TPO cell line. UT7TPO cells are a human megakaryoblastic cell line that express Tpo-R, whose survival and growth is dependent on the presence of TPO (Komatsu et al. *Blood* 1996, 87,4552).

Differentiation Assay

Likewise, some of the most preferred compounds of this invention were also positive in stimulating the maturation of megakaryocytes from human bone marrow cells. In this assay, purified human CD34+ progenitor cells were incubated in liquid culture with test compounds for 10 days and the number of cells expressing the transmembrane glycoprotein CD41 (gpIIb), a megakaryocytic marker, was then measured by flow cytometry (see Cwirla, S. E. et al Science, 1997, 276, 1696).

The pharmaceutically active compounds within the scope of this invention are useful as TPO mimetics in mammals, particularly humans, in need thereof.

Compounds of the invention also promoted the proliferation of UT7TPO and 32D-mpl cells at a concentration of 0.003 to 30 uM. Compounds of the invention also showed activity in the CD41 megakaryocytic assay at a concentration of 0.003 to 30 uM.

The present invention therefore provides a method of treating thrombocytopenia and other conditions with depressed platelet production, which comprises administering a compound of Formula (I) or a pharmaceutically acceptable salt, hydrate, solvate or ester thereof in a quantity effective to enhance platelet production. The compounds of Formula (I) also provide for a method of treating the above indicated disease states because of their demonstrated ability to act as TPO mimetics. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid;. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a TPO mimetic, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. Oral administration, which uses lower dosages is preferred. Parenteral administration, at high dosages, however, also can be used when safe and convenient for the patient.

Optimal dosages to be administered may be readily determined by those skilled in the art, and will vary with the particular TPO mimetic in use, the strength of the preparation, the mode of administration, and the advancement of the disease condition. Additional factors depending on the particular patient being treated will result in a need to adjust dosages, including patient age, weight, diet, and time of administration.

The method of this invention of inducing TPO mimetic activity in mammals, including humans, comprises administering to a subject in need of such activity an effective TPO mimetic amount of a pharmaceutically active compound of the present invention.

The invention also provides for the use of a compound of Formula (I) in the manufacture of a medicament for use as a TPO mimetic.

The invention also provides for the use of a compound of Formula (I) in the manufacture of a medicament for use in therapy.

The invention also provides for the use of a compound of Formula (I) in the manufacture of a medicament for use in enhancing platelet production.

The invention also provides for the use of a compound of Formula (I) in the manufacture of a medicament for use in treating thrombocytopenia.

The invention also provides for a pharmaceutical composition for use as a TPO mimetic which comprises a compound of Formula (I) and a pharmaceutically acceptable carrier.

The invention also provides for a pharmaceutical composition for use in the treatment of thrombocytopenia which comprises a compound of Formula (I) and a pharmaceutically acceptable carrier.

The invention also provides for a pharmaceutical composition for use in enhancing platelet production which comprises a compound of Formula (I) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat thrombocytopenia, including chemotherapy-induced thrombocytopenia and bone marrow transplantation and other conditions with depressed platelet production, or compounds known to have utility when used in combination with a TPO mimetic.

Contemplated Equivalents—It will be appreciated by the person of ordinary skill in the art that the compounds of Formulas I and II may also exist in tautomeric forms. For example, in Formula I, the double bond that is drawn between the two nitrogen atoms exists between the lower nitrogen atom and the 5-membered ring. Tautomeric forms of the compounds of Formulas I and II are exemplified by the following Formula (IV):

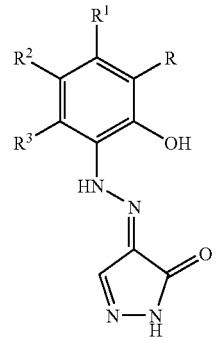

(IV)

where the 'R' groups are as defined above. All such compounds are included in the scope of the invention and inherently included in the definition of the compounds of Formulas I and II.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

EXAMPLE 1

Preparation of 3'-[N'-(1-cyclohexyl-3-methyl-5-oxo-1,5-dihydro-pyrazol-4-ylidene)-hydrazino]-2'-hydroxy-biphenyl-3-carboxylic acid a)
2-Cyclohexyl-5-methyl-2,4-dihydro-pyrazol-3-one Cyclohexylhydrazine hydrochloride (2.00 g, 13.3 mmol) and methyl acetoacetate (2.37 g, 20.4 mmol) were combined in glacial acetic acid (55 mL). The reaction was heated to 100° C. for 18 h. After allowing the reaction to cool to RT, the solvent was removed under reduced pressure to give 2.46 g of the desired product as a pale orange solid. This material was used without further purification. MS (ES+) m/z 181.2 (M+H$^+$).

b) 3'-[N'-(1-Cyclohexyl-3-methyl-5-oxo-1,5-dihydro-pyrazol-4-ylidene)-hydrazino]-2'-hydroxy-biphenyl-3-carboxylic acid To 3'-amino-2'-hydroxy-biphenyl-3-carboxylic acid hydrochloride (0.05 g, 0.19 mmol, prepared according to WO200189457) in EtOH (1 mL) and H$_2$O (1 mL) was added 3N HCl (0.13 mL, 0.23 mmol). The reaction was cooled to 0° C. and NaNO$_2$ (16 mg, 0.23 mmol) was added. After 15 min. at 0° C., a solution of the compound of Example 1(a) (0.03 g, 0.19 mmol) in EtOH (1 mL) was added. The reaction was adjusted to pH 8 with solid NaHCO$_3$ and stirred at room temperature. After 18 h, the reaction was adjusted to pH 3 with 3N HCl. The resulting precipate was collected and rinsed with hexane. Drying under vacuum gave 63 mg of the title compound as an orange solid. MS (ES+) m/z 421.2 (M+H$^+$).

EXAMPLE 2

Preparation of 5-(4-{N'-[1-(4-tert-butyl-cyclohexyl)-3-methyl-5-oxo-1,5-dihydro-pyrazol-4-ylidene]-hydrazino}-3-hydroxy-benzylidene)-thiazolidine-2,4-dione a) 5-(3-Hydroxy-4-nitrobenzylidene)-thiazolidine-2,4-dione

To a solution of 2,4-thiazolidinedione (3.50 g, 30.0 mmol) in ethanol (120 mL) was added 3-hydroxy-4-nitrobenzaldehyde (5.00 g, 30.0 mmol) and piperidine (0.44 mL, 4.50 mmol). The mixture was stirred at reflux for 15 hours and then cooled to 0° C. The resulting precipitate was collected and washed with cold ethanol to afford 3.53 g of the desired compound as a brown solid. Further concentration and precipitation of the mother liquor afforded an additional 3.1 g of the product. This was used without further purification in the next reaction. $^1$H NMR (CDCl$_3$)·8.20 (1H, d, J=8.8 Hz), 7.75 (1H, s), 7.26 (1H, s), 7.12 (1H, d, J=8.8 Hz).

b) 5-(4-Amino-3-hydroxybenzylidene)-thiazolidine-2,4-dione

To a solution of the compound of Example 2(a) (1.00 g, 3.50 mmol) in concentrated hydrochloric acid (45 mL) was added tin (II) chloride (2.00 g, 11.0 mmol). The mixture was heated to 80° C. for 1.5 h and then cooled to 0° C. The resulting precipitate was collected and rinsed with diethyl ether to afford 0.78 g of the desired compound. This was used without further purification. $^1$H NMR (DMSO)·10.3 (1H, br s), 7.59 (1H, s), 6.86-6.95 (3H, m).

c) 2-(4-tert-Butyl-cyclohexyl)-5-methyl-2,4-dihydro-pyrazol-3-one

To a solution of 4-tert-butylcyclohexanone (3.95 g, 25.6 mmol) in CH$_2$Cl$_2$ (50 mL) was added tert-butyl hydrazinecarboxylate (3.83 g, 25.6 mmol). A 1:1 mixture of MgSO$_4$/Na$_2$SO$_4$ was added to the reaction to make a slurry and the reaction was stirred vigorously. After 18 h, the reaction was diluted with CH$_3$CN and filtered. The solvent was removed from the filtrate under reduced pressure to give 6.78 g of N'-(4-tert-butyl-cyclohexylidene)-hydrazinecarboxylic acid tert-butyl ester as a white foam. This material was used without further purification in the next step. $^1$H NMR (400 MHz, DMSO-d$_6$) δ 9.51 (s, 1H), 2.93 (d, J=15 Hz, 1H), 2.30 (d, J=13 Hz, 1H), 2.08 (m, 1H), 1.89 (m, 2H), 1.66 (m, 1H), 1.43 (s, 9H), 1.25 (m, 1H), 1.13 (m, 1H), 1.03 (m, 1H), 0.85 (s, 9H).

To the crude product from above (6.78 g) in THF (150 mL) was added 10% Pd/C (20 mg). The material was hydrogenated using hydrogen at 50 psi for 18 h. After venting the hydrogen, the catalyst was removed by filtration and the solvent was removed under reduced pressure to give 7.61 g of N'-(4-tert-butyl-cyclohexyl)-hydrazinecarboxylic acid tert-butyl ester as a yellow oil. This material was used without further purification in the next step. MS (ES+) m/z 271.4 (M+H$^+$).

To the N'-(4-tert-butyl-cyclohexyl)-hydrazinecarboxylic acid tert-butyl ester (7.61 g) in CH$_2$Cl$_2$ (30 mL) was added TFA (10 mL). After 5 h at RT, the solvent was removed under reduced pressure. The residue was dissolved in glacial acetic acid (100 mL), methyl acetoacetate (4.46 g, 38.4 mmol) was added and the reaction was heated to 100° C. for 18 h. After allowing the reaction to cool to RT, the solvent was removed under reduced pressure. Flash chromatography of the residue (50% to 80% EtOAc/hexanes, silica gel) gave the two isomers of 2-(4-tert-butyl-cyclohexyl)-5-methyl-2,4-dihydro-pyrazol-3-one as pale yellow oils. Isomer 1: 2.67 g; TLC R$_f$ 0.30 (silica gel, 1:1 EtOAc/hexanes); MS (ES+) m/z 237.0 (M+H$^+$). Isomer 2: 0.66 g; TLC R$_f$ 0.15 (silica gel, 1:1 EtOAc/hexanes); MS (ES+) m/z 237.4 (M+H$^+$).

d) 5-(4-{N'-[1-(4-tert-Butyl-cyclohexyl)-3-methyl-5-oxo-1,5-dihydro-pyrazol-4-ylidene]-hydrazino}-3-hydroxy-benzylidene)-thiazolidine-2,4-dione To a solution of the compound of Example 2(b) (0.06 g, 0.23 mmol) in EtOH (0.5 mL) and H$_2$O (0.5 mL) was added 3N HCl (0.16 mL, 0.48 mmol). The reaction was cooled to 0° C. and NaNO$_2$ (19 mg, 0.28 mmol) was added. After 1.5 h at 0° C., a solution of the compound of Example 2(c) (isomer 1, 0.06 g, 0.23 mmol) in EtOH (1 mL) was added followed by solid NaHCO$_3$ until the reaction mixture was at pH 8. The reaction was heated to 60° C. for 18 h. After allowing the reaction to cool to RT, the 3N HCl was added until the mixture was at pH 3. The resulting precipitate was collected and rinsed with water. Flash chromatography (15% acetone/CHCl$_3$, silica gel) gave 26 mg of the title compound as an orange solid. MS (ES+) m/z 484.6 (M+H$^+$).

EXAMPLE 3

Preparation of 5-(4-{N'-[1-(4-tert-butyl-cyclohexyl)-3-methyl-5-oxo-1,5-dihydro-pyrazol-4-ylidene]-hydrazino}-3-hydroxy-benzylidene)-thiazolidine-2,4-dione In a manner analogous to Example 2(d), the compound of Example 2(b) (0.07 g, 0.30 mmol) and the compound of Example 2(c) (isomer 2, 0.7 g, 0.30 mmol) gave 10 mg of the title compound as an orange solid. MS (ES+) m/z 484.4 (M+H$^+$).

EXAMPLE 4

Preparation of (E)-3-{4-[1-(4-tert-butylcyclohexyl)-3-methyl-5-oxo-4,5-dihydro-1H-pyrazol-4-ylazo]-3-hydroxyphenyl}-2-methylacrylic acid a) (E)-3-(3-Hydroxy-4-nitrophenyl)-2-methylacrylic acid ethyl ester

3-Hydroxy-4-nitrobenzaldehyde (1.00 g, 5.98 mmol) and 2-(triphenyl-l$^5$-phosphanylidene)-propionic acid ethyl ester (2.60 g, 7.16 mmol) were combined in toluene (50 mL). After 18 h at reflux, the reaction was allowed to cool to RT and the solvent was removed under reduced pressure. The residue was subjected to flash chromatography (silica gel, 30% to 50% EtOAc/hexane) to give a yellow solid. This material was recrystallized from toluene to give 1.10 g of the desired material as yellow needles. MS (ES+) m/z 252.2 (M+H$^+$).

b) (E)-3-(3-Hydroxy-4-nitrophenyl)-2-methylacrylic acid

To the compound of Example 4(a) (0.50 g, 2.00 mmol) in THF (4 mL) was added 1N LiOH (4.40 mL, 4.40 mmol). After 5 h at RT, the reaction mixture was made acidic with 3N HCl. The resulting precipitate was collected, washed sequentially with $H_2O$ and hexanes and then dried under vacuum to give 0.23 g of the desired product as a yellow solid. This material was used without further purification. MS (ES+) m/z 224.4 $(M+H^+)$.

c) (E)-3-(4-Amino-3-hydroxy-phenyl)-2-methyl-acrylic acid ethyl ester hydrochloride The compound of Example 4(b) (0.23 g, 1.03 mmol) and $SnCl_2$ (0.59 g, 3.11 mmol) were combined in conc HCl (5 mL) and heated to 80° C. After 18 h, the reaction was allowed to cool to RT. The resulting precipitated was collected and rinsed with $Et_2O$ and dried to give 0.17 g of the desired compound as a white solid. This was used without further purification. 1H NMR (400 MHz, DMSO-d6) d 10.78 (broad s, 1H), 7.48 (s, 1H), 7.31 (m, 1H), 7.14 (s, 1H), 6.96 (dd, J=8.2; 1.4 Hz, 1H), 2.01 (s, 3H).

d) (E)-3-{4-[1-(4-tert-Butylcyclohexyl)-3-methyl-5-oxo-4,5-dihydro-1H-pyrazol-4-ylazo]-3-hydroxyphenyl}-2- methylacrylic acid To the compound of Example 4(c) (0.05 g, 0.22 mmol) in a mixture of EtOH (0.5 mL) and $H_2O$ (0.5 mL) was added 3N HCl (0.15 mL, 0.45 mmol). After cooling the reaction to 0° C., solid $NaNO_2$ (0.018 g, 0.26 mmol) was added and the suspension was stirred for 15 min. A solution of the compound of Example 2(c) (0.052 g, 0.22 mmol) in EtOH (1 mL) was added. Solid $NaHCO_3$ was added to bring the reaction to pH 8. After warming to RT, the reaction was allowed to stir for 18 h. The reaction mixture was made acidic (pH 3) with 3N HCl. The resulting precipitated was isolated, rinsed with $EtOH/H_2O$ (1:1 v/v) and dried under vacuum to give 0.046 g of the desired material as a red solid. MS (ES+) m/z 441.4 $(M+H^+)$.

EXAMPLE 5

Preparation of (E)-3-(4-{N'-3-Ethylcyclopentyl)-3-methyl-5-oxo-1,5-dihydropyrazol-4-ylidene]-hydrazino}-3-hydrophenyl-2-methylacrylic acid a) 3-Ethylcyclopentylhydrazine trifluoroacetate A mixture of (±)-3-ethylcyclopentanone (0.5 g., 4.46 mmol) and t-butyl carbazate (0.59 g., 4.46 mmol) in methylene chloride (25 mL) was stirred overnight at room temperature. The solution was evaporated and the residue taken up in a mixture of ethanol (100 mL) and 10% palladium on carbon (1.0 g.). The suspension was hydrogenated at 50 psi for 16 hours, filtered and evaporated. The residue was dissolved in methylene chloride (50 mL) and trifluoroacetic acid (10 mL) and stirred overnight. Evaporation of solvent gave 1.1 g of the title compound as a mixture of diastereomers. MS (ES+) m/z 129.3 $(M+H)^+$.

b) 2-(3-ethylcyclopentyl)-5-methyl-2,4-dihydroxy-pyrazol-3-one

A solution of the compound of Example 5(a) (1.1 g, 4.4 mmol) and methyl acetoacetate (0.53 g, 4.5 mmol) in methanol (50 mL) was heated at reflux under argon. After 16 hours, the solution was evaporated and the residue purified by flash silica chromatography (3% methanol/methylene chloride) to give 0.16 g of the title compound as a mixture of diastereomers. MS (ES+) m/z 195.2 $(M+H)^+$.

c) (E)-3-(4-{N'-3-Ethylcyclopentyl)-3-methyl-5-oxo-1,5-dihydropyrazol-4-ylidene}-hydrazino)-3-hydrophenyl-2- methylacrylic acid Sodium nitrite (0.07 g, 1.02 mmol) was added to a cold (0° C.), stirred solution of the compound of Example 4(b) (0.20 g, 0.77 mmol) in a mixture of 3N HCl (1.3 mL), ethanol (9.2 mL) and water (5.6 mL). The reaction was stirred for 10 minutes and then a solution of the compound of Example 5(b) (0.16 g, 0.82 mmol) in ethanol (2.0 mL) was added in one portion. Solid sodium bicarbonate was added to adjust the reaction to pH 8. The mixture was heated at 60° C. for 2 hours, kept overnight at room temperature and evaporated. A slurry of the resulting residue in water (20 mL) was neutralized with 0.5 N HCl and the mixture extracted with ethyl acetate (2×100 mL). The organic layers were dried ($Na_2SO_4$) and evaporated to give 0.11 g of the title compound as a mixture of diastereomers. MS (ES+) m/z 399.2 $(M+H)^+$.

EXAMPLE 6

Preparation of (E)-3-[4-(N'-{1-[3-(1,1-Dimethylpropyl)-cyclopentyl]-3-methyl-5-oxo-1,5-dihydropyrazol-4-ylidene}-hydrazino)-3-hydroxyphenyl]-2-methylacrylic acid a) 3-(1,1-Dimethylpropyl)-cyclopentylhydrazine trifluoroacetate In a procedure similar to Example 5(a), (±)-3-(1,1-Dimethyl-propyl)-cyclopentanone (1.0 g, 6.5 mmol) and t-butyl carbazate (0.86 g, 6.5 mmol) gave 1/s5g of the title compound as a mixture of diastereomers. MS(ES+) m/z 171.2 $(M+H)^+$.

b) 2-[3-(1,1-Dimethylpropyl)-cyclopentyl]-5-methyl-2,4-dihydroxypyrazol-3-one

In a procedure similar to Example 5(b), the compound of Example 6(a) (1.85 g, 6.5 mmol) and methyl acetoacetate (0.75 g, 6.5 mmol) gave 0.50 g of the title compound after purification by flash silica chromatography (2% methanol/methylene chloride). MS(ES+) m/z 237.4 $(M+H)^+$.

c) (E)-3-[4-(N'-{1-[3-(1,1-Dimethylpropyl)-cyclopentyl]-3-methyl-5-oxo-1,5-dihydropyrazol-4-ylidene}-hydrazino)-3-hydroxyphenyl]-2- methylacrylic acid In a procedure similar to Example 5(c), the compound of Example 6(b) (0.32 g, 1.35 mmol) and the compound of Example 4(b) (0.33 g., 1.27 mmol) gave 0.23 g of the title compound. MS(ES+) m/z 441.2 $(M+H)^+$.

EXAMPLE 7

Capsule Composition

An oral dosage form for administering a presently invented agonist of the TPO receptor is produced by filing a standard two piece hard gelatin capsule with the ingredients in the proportions shown in Table I, below.

TABLE I

| INGREDIENTS | AMOUNTS |
|---|---|
| 3'-[N'-(1-cyclohexyl-3-methyl-5-oxo-1,5-dihydro-pyrazol-4-ylidene)-hydrazino]-2'-hydroxy-biphenyl-3-carboxylic acid (Compound of Example 1) | 25 mg |
| Lactose | 55 mg |
| Talc | 16 mg |
| Magnesium Stearate | 4 mg |

EXAMPLE 8

Injectable Parenteral Composition

An injectable form for administering a presently invented agonist of the TPO receptor is produced by stirring 1.5% by weight of 5-(4-{N'-[1-(4-tert-butyl-cyclohexyl)-3-methyl-5-oxo-1,5-dihydro-pyrazol-4-ylidene]-hydrazino}-3-hydroxy-benzylidene)-thiazolidine-2,4-dione (Compound of Example 2) in 10% by volume propylene glycol in water.

EXAMPLE 9

Tablet Composition

The sucrose, calcium sulfate dihydrate and a presently invented agonist of the TPO receptor, as shown in Table II below, are mixed and granulated in the proportions shown with a 10% gelatin solution. The wet granules are screened, dried, mixed with the starch, talc and stearic acid; screened and compressed into a tablet.

TABLE II

| INGREDIENTS | AMOUNTS |
|---|---|
| 5-(4-{N'-[1-(4-tert-butyl-cyclohexyl)-3-methyl-5-oxo-1,5-dihydro-pyrazol-4-ylidene]-hydrazino}-3-hydroxy-benzylidene)-thiazolidine-2,4-dione; (Compound of Example 3) | 20 mg |
| calcium sulfate dihydrate | 30 mg |
| sucrose | 4 mg |
| starch | 2 mg |
| talc | 1 mg |
| stearic acid | 0.5 mg |

The compound 3'-[N'-(1-cyclohexyl-3-methyl-5-oxo-1,5-dihydro-pyrazol-4-ylidene)-hydrazino]-2'-hydroxy-biphenyl-3-carboxylic acid demonstrated an activity of, EC50=0.80 uM, 160% TPO in the above BaF3/hTPO-R proliferation assay.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound represented by the following Formula (I):

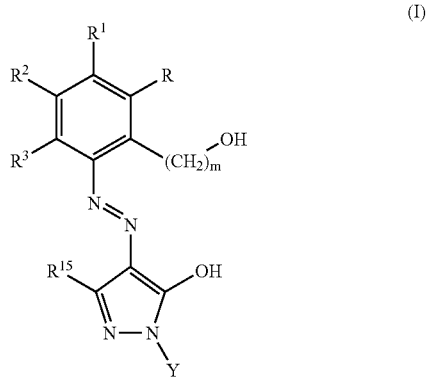

wherein:

$R$, $R^1$, $R^2$ and $R^3$ are each independently selected from hydrogen, $C_{1-6}$alkyl, $-(CH_2)_pOR^4$, $-C(O)OR^4$, formyl, nitro, cyano, halogen, aryl, substituted aryl, substituted alkyl, $-S(O)_nR^4$, cycloalkyl, $-NR^5R^6$, protected $-OH$, $-CONR^5R^6$, phosphonic acid, sulfonic acid, phosphinic acid, $-SO_2NR^5R^6$, a heterocyclic methylene substituent as represented by Formula (III),

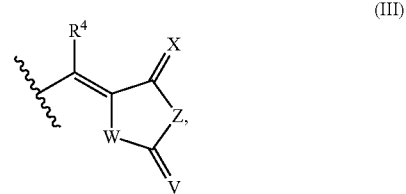

and a substituent as represented by Formula (VII),

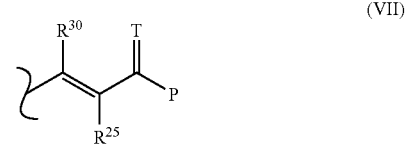

where, p is 0-6, n is 0-2,

W and Z are each independently selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, V and X are each independently selected from O, S and $NR^{16}$, where $R^{16}$ is selected from:

hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, $R^5$ and $R^6$ are each independently selected from hydrogen, alkyl, substituted alkyl, $C_{3-6}$cycloalkyl, and aryl, or $R^5$ and $R^6$ taken together with the nitrogen to which they are attached represent a 5 to 6 member saturated ring containing up to one other heteroatom selected from oxygen and nitrogen, T is selected from O, S and $NR^{16}$, where $R^{16}$ is selected from: hydrogen, alkyl, cycloalkyl, $C_1$-$C_{12}$aryl, substituted alkyl, substituted cycloalkyl and substituted $C_1$-$C_{12}$aryl, P is selected from $OR^4$, $SR^4$, $NR^5R^6$, and $R^4$, where $R^4$ is selected from: hydrogen, alkyl, cycloalkyl, $C_1$-$C_{12}$aryl, substituted alkyl, substituted cycloalkyl and substituted $C_1$-$C_{12}$aryl, $R^{25}$ is selected from: hydrogen, alkyl, cycloalkyl, $C_1$-$C_{12}$aryl, substituted alkyl, substituted cycloalkyl and substituted $C_1$-$C_{12}$aryl, and $R^{30}$ is selected from: hydrogen, alkyl, cycloalkyl, $C_1$-$C_{12}$aryl, substituted alkyl, substituted cycloalkyl and substituted $C_1$-$C_{12}$aryl;

$R^{15}$ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is a cyclic or polycyclic, unsaturated or saturated, non-aromatic ring containing from 3 to 16 carbon atoms and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —$C(O)OR^4$, —$C(O)NR^{10}R^{11}$, —$S(O)_2NR^{10}R^{11}$, —$S(O)_nR^4$ and protected —OH, where n is 0-2, $R^4$ is hydrogen, alkyl, cycloalkyl, $C_1$-$C_{12}$aryl, substituted alkyl, substituted cycloalkyl and substituted $C_1$-$C_{12}$aryl, and $R^{10}$ and $R^{11}$ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —$C(O)OR^4$, —$S(O)_nR^4$, —$C(O)NR^4R^4$, —$S(O)_2NR^4R^4$, nitro, cyano, cycloalkyl, substituted cycloalkyl, halogen, aryl, substituted aryl and protected —OH, or $R^{10}$ and $R^{11}$ taken together with the nitrogen to which they are attached represent a 5 to 6 member saturated ring containing up to one other heteroatom selected from oxygen and nitrogen, where $R^4$ is as described above and n is 0-2;

and pharmaceutically acceptable salts, and esters thereof;

provided that at least one of R, $R^1$, $R^2$ and $R^3$ is a substituted aryl group or a heterocyclic methylene substituent as represented in Formula (III) or a substituent as represented in Formula (VII).

2. A compound of claim 1 represented by the following Formula (II):

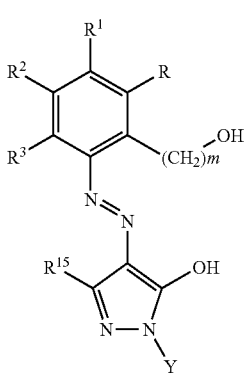

(II)

wherein:

R, $R^1$, $R^2$ and $R^3$ are each independently selected from hydrogen, $C_{1-6}$alkyl, —$(CH_2)_pOR^4$, —$C(O)OR^4$, formyl, nitro, cyano, halogen, aryl, substituted aryl, substituted alkyl, —$S(O)_nR^4$, cycloalkyl, —$NR^5R^6$, protected —OH, —$CONR^5R^6$, phosphonic acid, sulfonic acid, phosphinic acid, —$SO_2NR^5R^6$, a heterocyclic methylene substituent as represented by Formula (III),

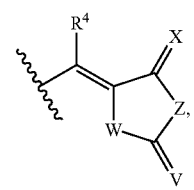

(III)

and a substituent as represented by Formula (VII),

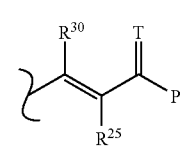

(VII)

where, p is 0-6, n is 0-2,

W and Z are each independently selected from O, S and $NR^{16}$, where $R^{16}$ is selected from:

hydrogen, alkyl, cycloalkyl, $C_1$-$C_{12}$aryl, substituted alkyl, substituted cycloalkyl and substituted $C_1$-$C_{12}$aryl, V and X are each independently selected from O, S and $NR^{16}$, where $R^{16}$ is selected from:

hydrogen, alkyl, cycloalkyl, $C_1$-$C_{12}$aryl, substituted alkyl, substituted cycloalkyl and substituted $C_1$-$C_{12}$aryl, $R^4$ is selected from: hydrogen, alkyl, cycloalkyl, $C_1$-$C_{12}$aryl, substituted alkyl, substituted cycloalkyl and substituted $C_1$-$C_{12}$aryl, $R^5$ and $R^6$ are each independently selected from hydrogen, alkyl, substituted alkyl, $C_{3-6}$cycloalkyl, and aryl, or R⁵ and R⁶ taken together with the nitrogen to which they are attached represent a 5 to 6 member saturated ring containing up to one other heteroatom selected from oxygen and nitrogen, T is selected from O, S and NR¹⁶, where R¹⁶ is selected from: hydrogen, alkyl, cycloalkyl, $C_1$-$C_{12}$aryl, substituted alkyl, substituted cycloalkyl and substituted $C_1$-$C_{12}$aryl, P is selected from OR⁴, SR⁴, NR⁵R⁶, and R⁴, where R⁴ is selected from: hydrogen, alkyl, cycloalkyl, $C_1$-$C_{12}$aryl, substituted alkyl, substituted cycloalkyl and substituted $C_1$-$C_{12}$aryl, R²⁵ is selected from: hydrogen, alkyl, cycloalkyl, $C_1$-$C_{12}$aryl, substituted alkyl, substituted cycloalkyl and substituted $C_1$-$C_{12}$aryl, and R³⁰ is selected from: hydrogen, alkyl, cycloalkyl, $C_1$-$C_{12}$aryl, substituted alkyl, substituted cycloalkyl and substituted $C_1$-$C_{12}$aryl;

R¹⁵ is selected from the group consisting of alkyl, $C_1$-$C_{12}$aryl, hydroxy, alkoxy, substituted alkyl, substituted $C_1$-$C_{12}$aryl and halogen;

m is 0-6; and

Y is a cyclic or polycyclic, unsaturated or saturated, non-aromatic ring containing from 5 to 14 carbon atoms and optionally substituted with one or more substituents selected from the group consisting of: alkyl, substituted alkyl, aryl, substituted cycloalkyl, substituted aryl, aryloxy, oxo, hydroxy, alkoxy, cycloalkyl, acyloxy, amino, N-acylamino, nitro, cyano, halogen, —C(O)OR⁴, —C(O)NR¹⁰R¹¹, —S(O)₂NR¹⁰R¹¹, —S(O)ₙR⁴ and protected —OH, where n is 0-2, R⁴ is hydrogen, alkyl, cycloalkyl, $C_1$-$C_{12}$aryl, substituted alkyl, substituted cycloalkyl and substituted $C_1$-$C_{12}$aryl, and R¹⁰ and R¹¹ are independently hydrogen, cycloalkyl, $C_1$-$C_{12}$aryl, substituted cycloalkyl, substituted $C_1$-$C_{12}$aryl, alkyl or alkyl substituted with one or more substituents selected from the group consisting of: alkoxy, acyloxy, aryloxy, amino, N-acylamino, oxo, hydroxy, —C(O)OR⁴, —S(O)ₙR⁴, —C(O)NR⁴R⁴, —S(O)₂NR⁴R⁴, nitro, cyano, cycloalkyl, substituted cycloalkyl, halogen, aryl, substituted aryl and protected —OH, or R¹⁰ and R¹¹ taken together with the nitrogen to which they are attached represent a 5 to 6 member saturated ring containing up to one other heteroatom selected from oxygen and nitrogen, where R⁴ is as described above and n is 0-2;

and pharmaceutically acceptable salts, and esters thereof; provided that at least one of R, R¹, R² and R³ is a substituted aryl group or a heterocyclic methylene substituent as represented in Formula (III) or a substituent as represented in Formula (VII).

3. A compound represented by Formula (II), as defined in claim 2, wherein:

R is a substituted aryl; and R¹ is hydrogen;

R is hydrogen; and R¹ is a substituted aryl;

R is a hydrogen; and R¹ is a substituent as represented in Formula (III); or

R is a hydrogen; and R¹ is a substituent as represented in Formula (VII);

and in each of the above cases:

R² and R³ are each independently selected from hydrogen, $C_{1-6}$alkyl, $C_{1-6}$alkoxy, nitro, cyano, halogen, aryl, substituted aryl, substituted alkyl, cycloalkyl, phosphonic acid, phosphinic acid and sulfonic acid;

R¹⁵ is selected from the group consisting of alkyl, substituted alkyl, $C_1$-$C_{12}$aryl, alkoxy and halogen;

m is 0-4; and

Y is selected from, cyclohexyl, cyclopentyl and cycloheptyl, where the cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;

and pharmaceutically acceptable salts, and esters thereof.

4. A compound represented by Formula (II), as defined in claim 2, wherein:

R is a substituted $C_1$-$C_{12}$aryl; and R¹ is hydrogen;

R is a hydrogen; and R¹ is a substituent as represented in Formula (III); or

R is a hydrogen; and R¹ is a substituent as represented in Formula (VII);

and in each of the above cases:

R² and R³ are each independently selected from hydrogen, $C_{1-6}$alkyl, $C_{1-6}$alkoxy, nitro, cyano, halogen, substituted alkyl and cycloalkyl;

R¹⁵ is selected from the group consisting of alkyl, substituted alkyl, $C_1$-$C_{12}$aryl, alkoxy and halogen;

m is 0-2; and

Y is selected from, cyclohexyl, cyclopentyl and cycloheptyl, where the cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;

and additionally, when R is a hydrogen; and R¹ is a substituent as represented in Formula (VII);

R²⁵ and R³⁰ are each selected from: hydrogen, $C_{1-6}$alkyl, $C_{1-6}$alkoxy, substituted $C_{1-6}$alkyl and cycloalkyl;

and additionally, when R is a hydrogen; and R¹ is a substituent as represented in Formula (VII); and when R is a hydrogen; and R¹ is a substituent as represented in Formula (III);

R⁴ is selected from: hydrogen, $C_{1-6}$alkyl, $C_{1-6}$alkoxy, substituted $C_{1-6}$alkyl and cycloalkyl;

and pharmaceutically acceptable salts, and esters thereof.

5. A compound represented by Formula (II), as defined in claim 2, wherein:

R is a substituted phenyl ring and R¹ is hydrogen; or

R is a hydrogen; and R¹ is a substituent as represented in Formula (III);

and in either of the above cases:

R² and R³ are each independently selected from hydrogen, $C_{1-6}$alkyl, substituted alkyl and halogen;

R¹⁵ is selected from the group consisting of $C_{1-4}$alkyl, $C_{1-4}$alkoxy, $C_1$-$C_{12}$aryl and halogen;

m is 0; and

Y is selected from, cyclohexyl, cyclopentyl and cycloheptyl, where cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;

and additionally, when R is a hydrogen; and R¹ is a substituent as represented in Formula (III);

R⁴ is selected from: hydrogen, $C_{1-6}$alkyl, $C_{1-6}$alkoxy, substituted $C_{1-6}$alkyl and cycloalkyl;

and pharmaceutically acceptable salts, and esters thereof.

6. A compound of claim 1 selected from:

3'-(1-Cyclohexyl-5-hydroxy-3-methyl-1H-pyrazol-4-ylazo)-2'-hydroxy-biphenyl-3- carboxylic acid;

3'-[1-(4-tert-Butyl-cyclohexyl)-5-hydroxy-3-methyl-1H-pyrazol-4-ylazo]-2'-hydroxy-biphenyl-3-carboxylic acid;

3'-[1-(3,4-Dimethyl-cyclohexyl)-5-hydroxy-3-methyl-1H-pyrazol-4-ylazo]-2'-hydroxy-biphenyl-3-carboxylic acid;

3'-[1-(3,4-Dichloro-cyclohexyl)-5-hydroxy-3-methyl-1H-pyrazol-4-ylazo]-2'-hydroxy-biphenyl-3- carboxylic acid;

5-[4-(1-Cyclohexyl-5-hydroxy-3-methyl-1H-pyrazol-4-ylazo)-3-hydroxy-benzylidene]-thiazolidine-2,4-dione;

5-{4-[1-(4-tert-Butyl-cyclohexyl)-5-hydroxy-3-methyl-1H-pyrazol-4-ylazo]-3-hydroxy-benzylidene}-thiazolidine-2,4-dione;

5-{4-[1-(3,4-Dimethyl-cyclohexyl)-5-hydroxy-3-methyl-1H-pyrazol-4-ylazo]-3-hydroxy-benzylidene}-thiazolidine-2,4-dione;

5-{4-[1-(3,4-Dichloro-cyclohexyl)-5-hydroxy-3-methyl-1H-pyrazol-4-ylazo]-3-hydroxy-benzylidene}-thiazolidine-2,4-dione;

(E)-3-{4-[1-(4-tert-butylcyclohexyl)-3-methyl-5-oxo-4,5-dihydro-1H-pyrazol-4-ylazo]-3-hydroxyphenyl}-2-methylacrylic acid;

(E)-3-(4-{N'-3-Ethylcyclopentyl)-3-methyl-5-oxo-1,5-dihydropyrazol-4-ylidene]-hydrazino}-3-hydrophenyl-2-methylacrylic acid; and (E)-3-[4-(N'-{1-[3-(1,1-Dimethylpropyl)-cyclopentyl]-3-methyl-5-oxo-1,5-dihydropyrazol-4-ylidene}-hydrazino)-3-hydroxyphenyl]-2-methylacrylic acid;

and pharmaceutically acceptable salts, and esters thereof.

7. A method of treating of thrombocytopenia in a mammal, including a human, in need thereof which comprises administering to such mammal a therapeutically effective amount of a compound of Formula (I), as described in claim 1.

8. A method as claimed in claim 7, wherein the mammal is a human.

9. A pharmaceutical composition for use in enhancing platelet production which comprises a compound of claim 1 and a pharmaceutically acceptable carrier.

10. A process for preparing a pharmaceutical composition containing a pharmaceutically acceptable carrier or diluent and an effective amount of a compound of the Formula (I) as described in claim 1 and pharmaceutically acceptable salts, hydrates, solvates and esters thereof which process comprises bringing the compound of the Formula (I) into association with the pharmaceutically acceptable carrier or diluent.

11. A process for preparing a compound of Formula (II) by reaction of a compound of Formula (XX)

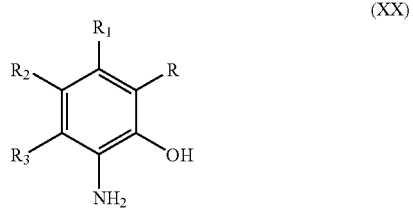

(XX)

or a protected form thereof with a compound of Formula (XXI) or tautomeric equivalent (XXII)

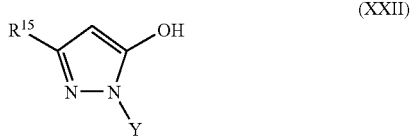

wherein
R is a substituted aryl; and $R^1$ is hydrogen;
R is hydrogen; and $R^1$ is a substituted aryl;
R is a hydrogen; and $R^1$ is a substituent as represented in Formula (III); or
R is a hydrogen; and $R^1$ is a substituent as represented in Formula (VII);
and in each of the above cases:
$R^2$ and $R^3$ are each independently selected from hydrogen, $C_{1-6}$alkyl, $C_{1-6}$alkoxy, nitro, cyano, halogen, aryl,.substituted aryl, substituted alkyl, cycloalkyl, phosphonic acid, phosphinic acid and sulfonic acid;
$R^{15}$ is selected from the group consisting of alkyl, substituted alkyl, $C_1$-$C_{12}$aryl, alkoxy and halogen;
m is 0-4; and
Y is selected from,
cyclohexyl, cyclopentyl and cycloheptyl, where the cyclohexyl, cyclopentyl and cycloheptyl are optionally substituted with from one to three substituents selected from the group consisting of: alkyl, substituted alkyl, $C_1$-$C_{12}$aryl, substituted $C_1$-$C_{12}$aryl, alkoxy and halogen;
followed if necessary or desired by salt formation.

12. A method of claim 7 wherein said thrombocytopenia is due to myelosuppression caused by chemotherapy or radiation therapy.

13. A method of claim 7 wherein said thrombocytopenia is due to an organ transplant.

14. A method of claim 7 wherein said thrombocytopenia is due to bone marrow, stem cell, or liver transplant.

15. A method of claim 7 wherein said thrombocytopenia is due to idiopathic thrombocytopenia purpura (ITP).

16. A method of claim 7 wherein said thrombocytopenia is due to myelodysplastic syndromes (MDS), aplastic anemia or leukemia.

17. A method of claim 7 wherein said thrombocytopenia is due to viral, fungal, microbial or parasitic infection.

18. A method of claim 7 wherein said thrombocytopenia is due to liver dysfunction.

19. A method of claim 7 wherein said thrombocytopenia is due to surgical procedures.

20. A method of claim 7 wherein said thrombocytopenia is due to treatment with antiviral or antibiotic agents.

21. A compound of claim 6 selected from:
3'-[N'-(1-cyclohexyl-3-methyl-5-oxo-1,5-dihydro-pyrazol-4-ylidene)-hydrazino]-2'-hydroxy-biphenyl-3- carboxylic acid;
or pharmaceutically acceptable salt, hydrate, solvate and ester thereof.

22. A compound of claim 1 selected from:

3'-(1-Cyclohexyl-5-hydroxy-3-methyl-1H-pyrazol-4-ylazo)-2'-hydroxy-biphenyl-3-carboxylic acid;

5-{4-[1-(4-tert-Butyl-cyclohexyl)-5-hydroxy-3-methyl-1H-pyrazol-4-ylazo]-3-hydroxy-benzylidene}-thiazolidine-2,4-dione;

(E)-3-{4-[1-(4-tert-butylcyclohexyl)-3-methyl-5-oxo-4,5-dihydro-1H-pyrazol-4-ylazo]-3-hydroxyphenyl}-2-methylacrylic acid;

(E)-3-(4-{N'-3-Ethylcyclopentyl)-3-methyl-5-oxo-1,5-dihydropyrazol-4-ylidene]-hydrazino}-3-hydrophenyl-2-methylacrylic acid; and (E)-3-[4-(N'-{1-[3-(1,1-Dimethylpropyl)-cyclopentyl]-3-methyl-5-oxo-1,5-dihydropyrazol-4-ylidene}-hydrazino)-3-hydroxyphenyl]-2-methylacrylic acid;

and pharmaceutically acceptable salts, and esters thereof.

* * * * *